(12) United States Patent
Arnold et al.

(10) Patent No.: US 12,090,085 B2
(45) Date of Patent: *Sep. 17, 2024

(54) COATED CONDOM

(71) Applicant: LRC PRODUCTS LIMITED, Berkshire (GB)

(72) Inventors: Andrew Richard Arnold, Bangkok (TH); Rohaida ABD Majid, Bangkok (TH); Tossaporn Tosanun, Samutpakran (TH)

(73) Assignee: LRC Products Limited, Berkshire (GB)

(*) Notice: Subject to any disclaimer, the term of this patent is extended or adjusted under 35 U.S.C. 154(b) by 377 days.

This patent is subject to a terminal disclaimer.

(21) Appl. No.: 17/113,696

(22) Filed: Dec. 7, 2020

(65) Prior Publication Data

US 2021/0085515 A1 Mar. 25, 2021

Related U.S. Application Data

(63) Continuation of application No. 14/359,492, filed as application No. PCT/GB2012/052983 on Dec. 3, 2012, now Pat. No. 10,857,026.

(30) Foreign Application Priority Data

Dec. 1, 2011 (GB) .................................. 1120679.4

(51) Int. Cl.
A61F 6/04 (2006.01)
A61F 6/00 (2006.01)

(52) U.S. Cl.
CPC ................ *A61F 6/04* (2013.01); *A61F 6/005* (2013.01); *A61F 2006/044* (2013.01)

(58) Field of Classification Search
CPC ...... A41D 19/00–0096; A41D 19/015–01594; A61F 6/00–24; A61B 42/00–60
See application file for complete search history.

(56) References Cited

U.S. PATENT DOCUMENTS 3,728,739 A    4/1973  Semp
3,810,458 A *  5/1974  Semp ................. A41D 19/0058
                                                    604/290

(Continued)

FOREIGN PATENT DOCUMENTS

CN    101188998 A    5/2008
EP     0147072 A1    7/1985

(Continued)

OTHER PUBLICATIONS

Namita Jindal et al., Microbial Polysaccharides in Food Industry, 2018, Biopolymers for Food Design, 8.1.1, https://www.sciencedirect.com/topics/agricultural-and-biological-sciences/xanthan-gum#:~:text=Xanthan%20is%20a%20long%2Dchain, 4.4). (Year: 2018).*

(Continued)

*Primary Examiner* — Michelle J Lee
(74) *Attorney, Agent, or Firm* — Dunlap Codding, P.C.

(57) ABSTRACT

A condom comprises, on one or more surfaces thereof, a self-lubricating coating comprising a dry powder having a particle size of 300 microns or less. The self-lubricating coating becomes lubricious when the coating comes into contact with a liquid environment. A method of making a self-lubricating condom comprises providing a dry condom and coating said condom, on one or more surfaces thereof, with a self-lubricating coating comprising a dry powder. The invention also provides the use of a dry powder such as xanthan gum to provide a self-lubricating coating for a condom.

22 Claims, 1 Drawing Sheet

(56) References Cited

U.S. PATENT DOCUMENTS

| | | | |
|---|---|---|---|
| 4,589,873 A | 5/1986 | Schwartz et al. | |
| 4,817,593 A | 4/1989 | Taller | |
| 4,829,991 A | 5/1989 | Boeck | |
| 5,292,534 A * | 3/1994 | Valentine | A61K 9/2077 424/457 |
| 8,256,609 B1 * | 9/2012 | Lee | A61F 6/005 206/484 |
| 10,857,026 B2 * | 12/2020 | Arnold | A61F 6/04 |
| 2002/0103414 A1 | 8/2002 | Harrison | |
| 2002/0182265 A1 * | 12/2002 | Burrell | A61P 1/00 424/618 |
| 2005/0037054 A1 * | 2/2005 | Hamann | A41D 19/0058 424/443 |
| 2005/0076917 A1 | 4/2005 | Wray et al. | |
| 2009/0028811 A1 | 1/2009 | Potter | |
| 2009/0163689 A1 * | 6/2009 | Cornish | A61F 6/04 264/215 |
| 2010/0012131 A1 | 1/2010 | Harrison | |
| 2012/0201748 A1 | 8/2012 | Cha | |

FOREIGN PATENT DOCUMENTS

| | | | |
|---|---|---|---|
| EP | 0860172 A2 | 8/1998 | |
| JP | 112021230 A | 1/1999 | |
| RU | 99102804 A | 1/2001 | |
| WO | WO89/04647 A1 | 6/1989 | |
| WO | WO-9201232 A1 * | 1/1992 | |
| WO | 1994015654 A1 | 7/1994 | |
| WO | 2006092585 A2 | 9/2006 | |
| WO | 2006100154 A1 | 9/2006 | |
| WO | 2009055652 A1 | 4/2009 | |

OTHER PUBLICATIONS

Office Action issued Apr. 13, 2021 in co-pending Russian Patent Application No. 2018109363/14(014415).

Search Report for corresponding International Application No. 2018109363/14(014415), mailed Apr. 13, 2021.

International Search Report and Written Opinion dated Mar. 11, 2013.

Combined Search and Examination Report in GB1120679.4 dated Mar. 14, 2012.

Delcour, Jan A. et al., Fibre-Rich and Wholegrain Foods: Improving Quality, Mar. 26, 2013. Woodhead Publishing, p. 108.

Office Action issued Aug. 20, 2021 in co-pending Russian Patent Application No. 2018109363(014415).

* cited by examiner

Process Flowchart
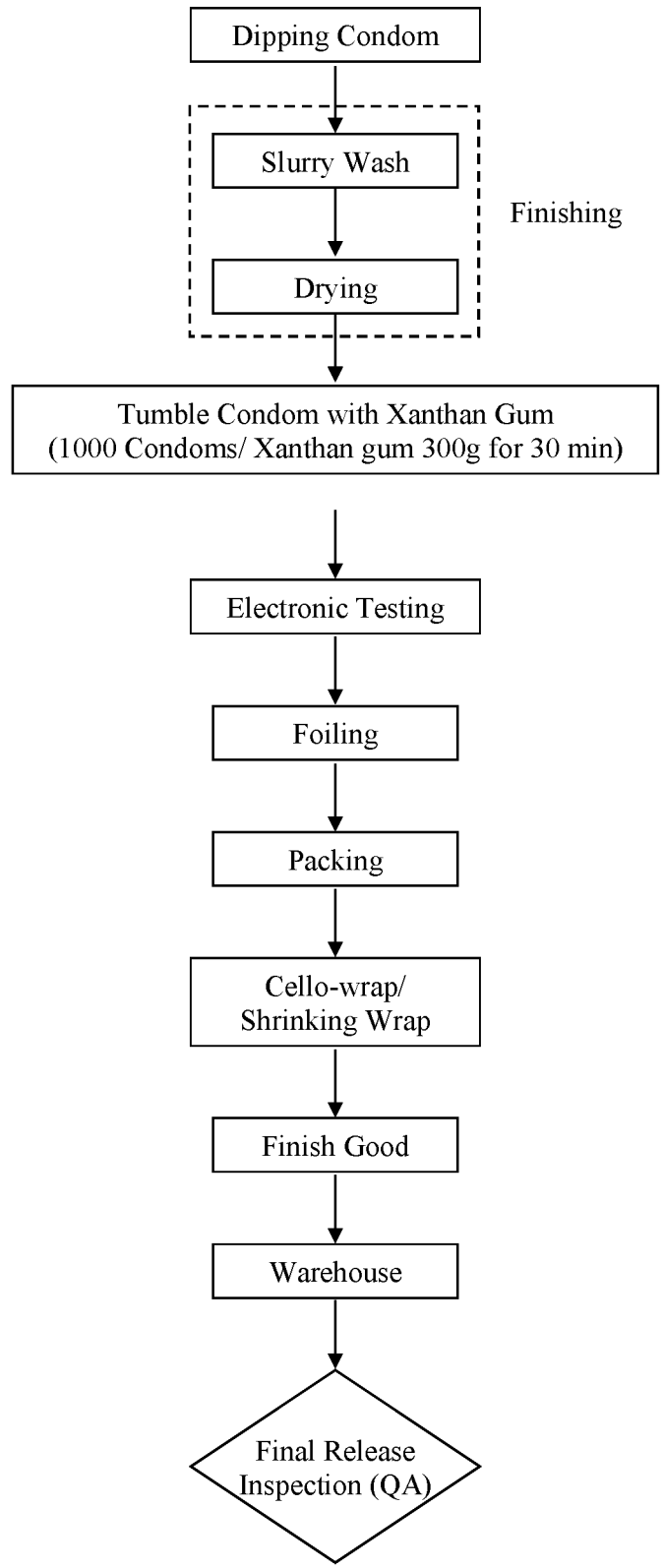

ced form of a traditional dusting powder, and include, for example, over 5% of an aqueous wetting solution (containing surfactant) and thus are aqueous and not dry. The powders are based on conventional dusting powders such as talc, silica, lycopodium, corn starch, carbonates, and the like. They are disclosed for use in combination with conventional liquid lubricants, and are said to improve the wetting ability of the conventional lubricant in terms of its ability to migrate (over time) along substantially the full length of a rolled condom. This document thus suffers from the same problems described above, since conventional lubricants must still be employed.

COATED CONDOM

CROSS-REFERENCE TO RELATED APPLICATIONS

This application is a continuation of U.S. patent application Ser. No. 14/359,492, filed 20 May 2014, which is a U.S. National Stage of International Application No. PCT/GB2012/052983, filed 3 Dec. 2012, which claims the benefit of GB 1120679.4, filed 1 Dec. 2011, all of which are herein fully incorporated by reference.

TECHNICAL FIELD

The present invention relates generally to condoms, in particular but not exclusively to coated condoms which have self-lubricating properties, to their use, and to a method of making them.

BACKGROUND

Condoms normally have a lubricant applied during manufacture which provides lubrication to the condom when in use, allowing in particular for additional vaginal lubrication. Such lubrication may be necessary (for example, to combat medical conditions) or is otherwise usually generally desirable. These added lubricants are typically in a liquid or gel form and are normally silicone oil or water-based lubricants. The lubricant when applied to the condom can either be applied to the rolled condom, leaving the lubricant to migrate over time throughout the condom on both sides, or alternatively, the lubricant can be applied to the unrolled condom to ensure it is well distributed along the condom length prior to rolling and packing. Various other similar coatings are also known, and these are typically aqueous based, and in liquid or gel form. However, we have now appreciated that such added lubricants or coatings, whether based on silicone, polyethylene glycol (PEG) or aqueous based, are often perceived as 'messy' or 'sticky' when the consumer opens the pack and dons the condom.

WO 2008/011088 describes a therapeutic, moisturising coating composition for elastomeric articles which transfers as a "lotion" to the user during use of the article. The composition, which can be applied to the surface of the articles, is said to be particularly useful in examination and surgical gloves, and provides topical benefits, such as moisturisation, to the skin. The composition comprises at least 10% by weight glycerin and some sorbitol and, although non aqueous, is essentially in the form of a viscous cream or gel when present on the article at room temperature. Such a composition does not address the problem described above.

WO 2006/092585 describes a personal lubricant composition which may be used with condoms, and which comprises a mixture of a latent lubricant additive and a carrier lubricant in which the latent lubricant additive is insoluble. The only lubricant additive disclosed is poly(ethylene oxide), and the lubricant composition is of a viscous nature, having a pituity similar to that of natural mucous. These gel like compositions contain large amounts of glycerol and propylene glycol, and although lubricious, suffer from the drawback of producing a condom which may be perceived as messy or sticky by the user during the unpacking and donning process.

WO 2006/049627 discloses a composition comprising a powder coated with an aqueous composition comprising a surfactant, and the composition may be used with condoms. These "surfactant-modified" powders are essentially a modi- Various other sorts of liquid or gel-like lubricants or coatings are described in publications JP 08-020528, JP 2003245294, JP 2002102267, JP11021230, JP 9323941.

Dusting or finishing powders for condoms and different elastomeric articles such as gloves are also known. These are typically based on compounds such silica, talc, carbonates, cornstarch and the like, and are used to prevent the surfaces of the article from sticking to each, or to another similar article; and to assist with donning. Such powders are, for example, described in publications WO 2005/016284, EP 1519762, U.S. Pat. Nos. 4,143,423, and 4,059,097. Surgical and examination gloves can also be provided with coatings intended to provide increased slip, and examples of these are described, for example, in EP 678036 and JP 5123641.

WO 89/01324 describes a natural feeling condom designed to provide more stimulation for the male by allowing the penis to slide relative to the condom. This is achieved by stabilising the condom relative to the vagina by adhering or bonding the outer surface of the condom to the vagina using a multiplicity of minute fibres or a friction enhancing agency. The friction enhancing agent is generally held within a viscous matrix which is bonded to the surface of the condom. The condom is longer than normal condoms to allow for folds to form during use, thus increasing friction for the male.

However, none of the above publications addresses the problem of the perceived stickiness or messiness of a condom by the user during the unpacking and donning process. Having appreciated the above, we have now devised a way of substantially avoiding or minimising this problem.

BRIEF DESCRIPTION OF THE DRAWING

The FIGURE shows a process flowchart illustrating one embodiment of the present invention.

SUMMARY OF THE INVENTION

According to one aspect of the present invention, there is provided a condom comprising, on one or more surfaces thereof, a self-lubricating coating comprising a dry powder having a particle size of 300 microns or less.

A self-lubricating coating as defined herein is one which is capable, upon contact with an aqueous environment, of increasing its lubricity so as to provide a lubricious or slippery coating. Preferably, the self-lubricating coating is substantially non-lubricious when in the dry state.

Thus, in another aspect, there is provided a condom comprising, on one or more surfaces thereof, a self-lubricating coating comprising a dry powder having a particle size of 300 microns or less, which coating becomes lubricious when the coating comes into contact with an aqueous environment.

In another aspect of the invention, there is provided a method of making a self-lubricating condom, which method comprises providing a dry condom and coating said condom, on one or more surfaces thereof, with a self-lubricating coating comprising a dry powder having a particle size of 300 microns or less. The method of the invention encompasses making a condom according to the invention as described herein.

A "lubricious" surface or coating is one having a low coefficient of friction (for example, compared to an uncoated and otherwise untreated elastomeric film surface), and generally demonstrates properties similar with standard marketed lubricated condoms. The self-lubricating coating, which is suitably dry, is preferably substantially non-lubricious when in a dry state. By "non-lubricious" is meant that the coating is non-sticky as judged by the user, and suitably does not provide any appreciable degree of slip until it comes into contact with a moist or aqueous environment such as that provided by vaginal secretions. An aim of the invention is to provide a "non-sticky" or "non-messy" condom which remains as such until the condom has been donned and is ready for use.

The dry powder is preferably water-soluble or substantially water-soluble.

Advantageously, as the moisture level increases on or around the self lubricating condom, the coating moves from a dry state, to a tacky state and to a lubricious state. The tacky state is particularly advantageous on the interior of the condom as the tackiness aids in maintaining the condom on the penis once donned. Therefore according to yet a further embodiment of the present invention there is provided a condom comprising a self-lubricating coating which includes a dry powder having a particle size of 300 microns or less, the coating being arranged substantially on the interior surface of the condom.

The self lubricating coating may therefore advantageously have two effects, namely providing a tacky lubrication on the interior when in contact with the relatively lower moisture environment when donned on a penis, whereas in the relatively higher moisture environment of vaginal fluid or the like, the coating becomes substantially slippery or lubricious Suitably, the dry powder (for example, based on xanthan gum) is capable of absorbing a quantity of water to transform it to a hydrated, lubricious state, thus providing lubrication "in situ".

Preferred dry powders include powders comprising, or consisting of, xanthan gum, one or more polysaccharides, pullulan, one or more polyacrylamides, carrageenan, *aloe vera*, or mixtures of two or more of the above. A particularly preferred powder includes xanthan gum.

The self-lubricating coating is preferably dry and may comprise a dry powder and one or more inert ingredients (which are also preferably dry), or may consist of, or consist essentially of, the dry powder itself.

Thus, in another aspect the invention provides a dry condom comprising, on one or more surfaces thereof, a dry powder which becomes lubricious when the coating comes into contact with a liquid environment, the dry powder having a particle size of 300 microns or less. The liquid environment is preferably aqueous or aqueous-based. The dry powder is suitably substantially non-lubricious when in a dry state, so as to minimise any perception of stickiness by the user which is typical of many condoms known in the art. The dry powder is preferably water-soluble and preferably comprises, or consists of, xanthan gum, one or more polysaccharides, pullulan, one or more polyacrylamides, carrageenan, *aloe vera*, or mixtures of two or more of the above. A particularly preferred powder comprises xanthan gum.

The condom, which comprises the basic sheath of elastomeric material, is also preferably dry, in addition to the self-lubricating coating which is coated thereon.

The condom of the invention is preferably free of lubricant, in particular any lubricant in liquid or gel form, apart from the self-lubricating coating itself. Thus conventional lubricants such as oil-based or water-based lubricants are preferably not present.

Any suitable amount of coating may be used on the condom, although typically the weight of the coating is from 0.005 g to 0.5 g per condom, preferably no more than about 0.07, further preferably no more than 0.05 g per condom. A preferred range for the powder coating is 0.01 g to 0.07 g per condom. It has been found coatings lower than 0.005 g may provide insufficient lubrication during use. If the coating level exceeds the upper limit claimed herein the powder may not fully dissolve, (leaving excess powder), has potential to cause abrasion of the skin or irritation during use, or even cause damage to the integrity of the condom.

Preferably, the step of coating the condom comprises tumbling the dry condom with a self-lubricating coating as described herein. The tumbling is preferably dry tumbling In another aspect, the invention also provides a package comprising a condom according to the invention. The package is preferably a foil package and, other than the self-lubricating coating on the condom, is preferably free of any lubricant, particularly lubricant in a liquid or gel-like state.

In another aspect, the invention also provides the use of a dry powder to provide a self-lubricating coating for a condom.

In this aspect, preferably the self-lubricating coating becomes lubricious when the coating comes into contact with a liquid environment, such as an aqueous or an aqueous-based environment. The self-lubricating coating is preferably substantially non-lubricious when in a dry state.

The dry powder preferably comprises, or consists of, xanthan gum, or may alternatively, or in addition, comprise, or consist of, one or more polysaccharides, pullulan, one or more polyacrylamides, carrageenan, *aloe vera*, or mixtures of two or more of the above.

The present invention thus encompasses the use of a dry powder which is non-messy or non-sticky and can be applied to the condom during processing. The condom then becomes lubricious in contact with aqueous environments such as vaginal fluids during coitus, thus providing lubrication. That is, the dry power, which when dry does not provide any significant degree of slip or lubriciousness, becomes lubricious when wet. The main advantage of this feature is that the end user does not experience a sticky or messy condom when opening the foil and donning the condom.

The FIGURE shows a process flowchart illustrating one embodiment of the present invention.

Any suitable condom may be used as the basic condom component of the present invention, provided that the object of achieving a lubricious coating can be attained. We have found that a variety of different kinds of condom, whether natural or synthetic, may be used as desired.

As will be clear to those skilled in this field, condoms may be manufactured from a variety of materials including natural substances such as natural rubber latex, or synthetic materials. For example, synthetic materials include carboxylated rubbers, such as carboxylated styrene-butadiene rubber and carboxylated acrylonitrile-butadiene rubber; nitrile rubbers, such as nitrile-butadiene rubber; polyurethane, and synthetic polyisoprene. These materials may be used either individually, or two or more may be blended depending upon the characteristics required. Useful blends include those where natural rubber latex is blended with one or more synthetic materials—for example, a blend of natural rubber and polyurethane. Preferably, a condom made from natural rubber latex, or comprising a natural rubber latex base, is used.

The condom itself may be manufactured in any suitable way. Typically, this is done by dipping a condom-shaped former into a latex or latex blend to form a film which is subsequently dried and cured. It will be understood that the manufacture of suitable rubber latexes, and the subsequent formation of condoms therefrom, are well understood procedures to those skilled in this particular art.

The finished condom sheath is then coated with a self-lubricating coating as described further below. In use, the coating on the condom surface (preferably on both the inner and outer surfaces) will come into contact with a liquid, preferably aqueous, environment, such as provided by vaginal secretions or saliva, or other synthetic liquid or aqueous products. The coating then becomes lubricious in response to this contact, and this provides lubrication, or additional lubrication, during coitus. Lubricity is a well known characteristic in this particular field, and essentially relates to the amount of slip provided by a surface or coating. A lubricious surface or coating will have a low coefficient of friction (for example, compared to an uncoated and otherwise untreated elastomeric film surface), and generally demonstrate stringy and mucous-like behaviour.

Any suitable dry powder may be used to form the self-lubricating coating, provided that the powder is biocompatible with mucous membranes and does not damage condoms during tumbling or subsequent processing and storage.

A preferred powder comprises xanthan gum. Xanthan gum is a high molecular weight polysaccharide gum, containing D-glucose and D-mannose as the dominant hexose units, along with D-glucuronic acid. It is normally prepared as the sodium, potassium, or calcium salt, and typically has a molecular weight of around $2 \times 10^6$. It is generally produced by aerobic fermentation of a carbohydrate source using, for example, *Xanthamonas campestris*. Any suitable type of xanthan gum may be used, and suitably the gum is provided in particulate (ie powder) form. Transparent (ie clear) xanthan gum is a preferred kind, suitably transparent, particulate xanthan gum. Desirably, the xanthan gum is soluble in hot water and cold water. Suitable gums include those available from CP Kelco (headquartered in Atlanta, Georgia, USA). A preferred type are those available under the tradename Keltrol®, with the Keltrol® cosmetic grade (CG) products being particularly preferred. These are high quality powders with a low bacterial count. Examples of suitable powders include Keltrol® cosmetic grade-T (CG-T), which is a transparent powder; and Keltrol® cosmetic grade-F (CG-F) which is a fine powder product.

Other suitable xanthan gum products include those available from Bestessen Natural Ltd (Shandong, China). The Food Grade (FG) gums are preferred, and useful examples include Natraxan® FG-HD, which is a quick dispersible gum, and Natraxan® FG200 which is a fine powder product.

Other suitable powders which may be used include those comprising polysaccharides, in particular high molecular weight polysaccharides and homopolysaccharides, for example homopolysaccharides of glucose. Polysaccharides and homopolysaccharides having a molecular weight of about 10 KDa or higher are preferred, including, for example, those having a molecular weight of about 50 KDa or above, or 100 KDa or above. Any suitable polysaccharide may be used, provided that the powder is biocompatible with mucous membranes and does not damage condoms during tumbling or subsequent processing and storage. A suitable example is pullulan, which is a linear homopolysaccharide polymer consisting of maltotriose units. Pullunan is produced from starch by the fungus *Aureobasidium pullulans*.

Other suitable powders which may be used include those comprising polyacrylamide, a polymer formed from acrylamide subunits. An ionic polyacrylamide, for example an anionic polyacrylamide (for example those incorporating some acrylic acid), may be used if desired. Suitable examples include the polyacrylamide products available from Ciba Speciality Chemicals under the Magnafloc® range. These are anionic polyacrylamides in the form of free-flowing granular powders. A suitable example includes the product Magnofloc® LT 27 AG, which is a high-molecular weight anionic polyacrylamide. Again, any suitable polyacrylamide may be used, provided that the powder is biocompatible with mucous membranes and does not damage condoms during tumbling or subsequent processing and storage.

Other suitable powders which may be used include those comprising carrageenan. Carrageenan is a cell wall hydrocolloid found in certain species of seaweeds belonging to red algae, and it can be extracted therefrom. A preferred type is carrageenan comprising sulphated polysaccharides and extracted from red seaweed. Suitable carrageenan products include those available from CP Kelco under the Genu® range. A preferred type is Carrageenan CG-129. Again, any suitable carrageenan may be used, provided that the powder is biocompatible with mucous membranes and does not damage condoms during tumbling or subsequent processing and storage.

Other suitable powders include those based on extracts from the *Aloe vera* plant, which extracts are collectively commonly known by the same name as the plant. Freeze dried *Aloe vera* in particulate form is preferred.

Normal dusting powders such as corn starch, silica and carbonates are generally not suitable powders for producing a self-lubricating coating, because they are not readily soluble in aqueous environments so as to produce lubricious coatings.

Preferably, if desired, the condom or the powder or the coating does not comprise poly(ethylene oxide); or glycerol; or polyethylene glycol; or squalene, its partial hydrolyzate or squalane.

We prefer to use a powder having a small particle size, and typically the powder will have an average particle size of less than about 200 microns, preferably about 180 microns or less. Smaller particle sizes may also be used, for example about 100 microns or less. In particular, we have found xanthan gum powders, and polysaccharide powders, particularly high molecular weight polysaccharide powders, having a particle size of about 180 microns (or less) to give good results. For example, the particle size of Keltrol CG-T and Ketrol CG-F are approximately 180 microns and 75 microns respectively. Powders with a particle size of about 180 microns or less have been found to provide high lubricity on condoms, and such condoms also meet the criteria set out in ISO 4074:2002 and ISO 23409:2011 with respect to initial and pre-determined ageing conditions through out product's shelf life.

A preferred process according to the present invention is shown schematically in the FIGURE. A condom is produced by dipping a condom-shaped former or mandrel into a latex or latex blend to form a thin film which is subsequently dried and, if desired, cured or vulcanised with heat or chemical treatments. Typically, the process includes a washing step in which the condom is washed in a slurry of aqueous carbonate solution (eg aqueous calcium carbonate). Preferably, the film is then dried so as to remove all moisture. It is a particularly preferred feature of the invention that the condoms are completely dry before being subsequently coated.

Once the finished condom sheaths have been manufactured, a quantity of these dry condoms is placed in a tumbler, and a quantity of coating or dry powder such as particulate xanthan gum is added. The condoms and powder are then tumbled together for a chosen period—typically for 20 to 30 minutes. The process serves to coat the condom with the powder, and a certain quantity of the powder will adhere naturally to the inner and outer surfaces of the condoms so as to provide a substantially uniform coating on all surfaces.

It is a preferred feature of the invention that the tumbling process is carried out in a dry environment—that is, both the condoms and coating or powder are introduced in the dry state and the tumbler apparatus itself does not introduce any moisture.

The coated condoms may then be removed from the tumbler and tested for defects using standard quality control procedures. Typically, electronic testing (ET) and/or water testing are used to check for any defects (such as holes) in the condom film, and defective condoms discarded as required.

The condoms may then be packaged (ie foiled) in the usual way.

The coating may be applied to the condom sheath using any suitable technique, but a preferred method is the tumbling process. Other methods of coating the condom include, but are not limited to, electrostatic spraying, powder flocking or any other application method used to coat dry powder on the condom surface.

Generally, the tumbling method is a process that applies a coating or coating composition in a liquid or solid state onto an elastomeric surface such as a condom by placing the condoms into a tumbler apparatus and then introducing into the tumbler either the liquid composition coating or a solid coating composition such as a powder. In the present invention, the coating is introduced in the dry, solid state, preferably as a powder. The condoms are then tumbled with the coating for a desired period of time.

In a preferred aspect, the condoms are tumbled with the chosen powder only, without the addition of, or need for, other carriers or components. However, more than one dry powder may be used if desired, although generally a single powder is employed.

The tumbler apparatus may comprise any suitable design, but will generally comprise a large circular drum which may be rotated about a central axis at a chosed revolution speed. As will be understood, the speed of revolution of the drum (in rpm) and the temperature of the tumbling may be selected as desired by the operator, depending upon the type of powder being used. We typically prefer to tumble the condoms for one cycle of about 30 minutes at ambient temperature (for example 20-25° C.), although any suitable conditions may be used. Preferably, the tumbling conditions are chosen so as to produce a substantially uniform coating on both the inside and outside surfaces of the condom.

In a preferred aspect of the process, from about 5 g to about 500 g of powder (for example, xanthan gum) is used per 1000 dry condoms, typically 50 g to about 500 g. However a desired amount is in the range 100-500 g per 1000 dry condoms. The condoms are tumble dried with the dry powder (such as xanthan gum) in a conventional tumbling apparatus. Any suitable tumbling time may be used, but typically a period of about 30 minutes is suitable. Preferably, the process is carried out at ambient temperature—for example from 20-25° C.

For example, 9600 condoms that have passed QC inspection are placed inside the tumble drum. 4800 g of xanthan gum is then placed inside the tumble drum and tumbled for about 30 minutes at ambient temperature.

The condoms are thus coated with the powder. We have found that an optimum level of coating, particularly with xanthan gum, can be obtained whilst using about 300 g of powder per 1000 condoms, although it will be appreciated that this will vary depending upon the type of condom and powder used.

After this period the tumbling is stopped and sufficient powder has been attached to the inner and outer side of the condom. The condom is essentially dry and can be processed through electronic testing and foiling as is standard practice for those skilled in the art.

Preferably, no additional lubricant is added to the foil package containing the condom. Generally, additional lubrication of this kind will not be necessary for the condoms of the invention. However, it is envisaged that package may further includes a liquid or gel like lubricant.

It is further envisaged that one or more enhancement actives may be added to or be present in the coating. Enhancement actives are preferably in powder form, although it is also envisaged that they may be gels and/or liquids. Enhancement actives preferably include one or more of a performance enhancing active such as a desensitising agent or vasodilator (for example benzocaine retardant cream or glyceryl trinitrate), a sensory effect active (that provides a sensation feeling of cooling, tingling or warming), or a flavour enhancing active The following example illustrates the present invention.

EXAMPLE

Four different types of xanthan gum were selected for testing. They are Keltrol® CG-T and CG-F and the FD-HD and FG200 products available from Bestessen Natural Ltd. These powders were tested under various tumbling conditions. Either 200 g or 500 g of powder was used per 1000 condoms, and the tumbling time was varied between 10 and 30 minutes. For each test, 1000 dry condoms were tumble dried with either 200 g or 500 g of the selected powder for up to 30 min in a conventional tumbling apparatus. Batches of 30 condoms were removed at intervals of 10, 20 and 30 minutes.

The amount of powder adhered to the condoms after tumbling for the selected time period was measured. On average, an amount of powder ranging between about 0.09 g and 0.22 g was deposited per condom. It is particularly preferred to be in the range 0.01 g and 0.12 g.

Each batch was further tested in order to determine the integrity of the condom film, in particular to check for damage to the film such as small holes. Both standard electrical testing (ET) and water testing were carried out according to conventional techniques, and the results are shown in Table 3.

The ET and Water Tests are conducted in accordance with Annex L of ISO 4074:2002. Brief details of the tests are given below.

Water Test: filling of the condom with water 300+/−10 $cm^3$ at a temperature between 10 and 40° C. Inspect the condom for visible signs of leakage. A failure is deemed to be any condom exhibiting visible signs of leakage from holes more than 24 mm+/−1 mm from the open end of the condom. In the absence of any leakage the condom is then rolled (at least one revolution) on coloured absorbent paper.

Electrical Test (ET): Fit the open end of the condom on to the mount of the Electrical Tester. Add 200+/−10 ml electrolyte (consisting of an aqueous sodium chloride solution), and inspect for visible electrolyte leakage. Deem as failed any condom which exhibits visible leakage. Submerge the non-leaking condom in a container also containing electrolyte (at least 25 mm from open end of condom is submerged). Apply 10V stabilized continuous voltage source in series with 10 kohm high precision electrical resistance between the electrode in the container and the electrode inside the condom. Measure the voltage at the resistor after 10+/−2 secs.

If a voltage equal to or greater than 50 Mv, empty the condom and subject the condom to Water Test.

What is claimed is:

1. A condom comprising:
   an interior surface of the condom;
   an exterior surface of the condom, wherein the exterior surface of the condom is dry; and
   a dry self-lubricating coating on at least a portion of the exterior surface, the dry self-lubricating coating consisting of a dry polymer powder having a particle size of between 75 and 300 microns;
   wherein the self-lubricating coating is non-lubricious when in a dry state and becomes lubricious when in contact with a liquid environment, and
   wherein the dry powder polymer is selected from the group consisting of a polysaccharide, pullulan, a polyacrylamide, carrageenan, xanthan gum, and combinations thereof.

2. A package comprising the condom according to claim 1, optionally wherein the package comprises foil.

3. The package according to claim 2, wherein the package is free of any lubricant in a liquid or gel state.

4. The package according to claim 2, further comprising a liquid or gel lubricant.

5. The condom according to claim 1, wherein the dry polymer powder has a particle size of between 75 and 200 microns.

6. The condom according to claim 5, wherein the dry polymer powder has a particle size of between 75 and 100 microns.

7. The condom according to claim 1, further comprising one or more enhancement actives in powder form present on the interior and/or exterior surface of the condom.

8. The condom according to claim 7, wherein one of the one or more enhancement actives is a performance enhancing active, a sensory effect active, a flavour enhancing active, a desensitising agent, or a vasodilator.

9. The condom according to claim 1, wherein the liquid environment is aqueous or aqueous-based.

10. The condom according to claim 1, wherein the condom is dry.

11. The condom according to claim 1, wherein the dry polymer powder is water-soluble.

12. The condom according to claim 1, wherein the dry polymer powder consists of xanthan gum.

13. The condom according to claim 1, wherein the dry polymer powder consists of pullulan or carrageenan.

14. The condom according to claim 1, wherein the dry polymer powder consists of a high molecular weight polysaccharide with a molecular weight of 10 KDa or more.

15. The condom according to claim 1, wherein the condom is free of lubricant or is free of oil-based or water-based lubricants.

16. The condom according to claim 1, wherein a weight of the dry self-lubricating coating is from 0.005 g to 0.5 g per condom.

17. A method of making a self-lubricating condom comprising:
   providing a condom having an interior surface and an exterior surface, wherein the exterior surface of the condom is dry; and
   coating a dry self-lubricating coating on at least a portion of the dry exterior surface of the condom, the self-lubricating coating consisting of a dry polymer powder having a particle size of between 75 and 300 microns, wherein the dry self-lubricating coating is present in a dry state on the dry exterior surface of the condom and is non-lubricious in that state; and
   wherein the dry polymer powder is selected from the group consisting of a polysaccharide, pullulan, a polyacrylamide, carrageenan, xanthan gum, and combinations thereof.

18. The method according to claim 17, wherein the coating step comprises tumbling the condom with the dry self-lubricating coating.

19. The method according to claim 18, wherein the tumbling is dry tumbling.

20. The method according to claim 18, wherein the tumbling is carried out for from 15 to 45 minutes.

21. The method according to claim 17, wherein the coating step comprises a step selected from the group consisting of electrostatic spraying and powder flocking.

22. The method according to claim 17 further comprising using from 5 g to 500 g of the dry polymer powder per 1000 condoms.

* * * * *